United States Patent
Kawasaki et al.

[11] Patent Number: 6,066,858
[45] Date of Patent: May 23, 2000

[54] AUTORADIOGRAPHIC PROCESS

[75] Inventors: Motoko Kawasaki, Tokyo; Katsumi Hayashi; Masashi Hakamata, both of Kanagawa; Keiji Mori, Tokyo, all of Japan

[73] Assignee: Fuji Photo Film Co., Ltd., Kanagawa, Japan

[21] Appl. No.: 08/982,102

[22] Filed: Nov. 17, 1997

Related U.S. Application Data

[63] Continuation of application No. 08/667,283, Jun. 20, 1996, abandoned, which is a continuation of application No. 08/509,654, Jul. 31, 1995, abandoned, which is a continuation of application No. 08/353,339, Dec. 5, 1994, abandoned, which is a continuation of application No. 08/114,625, Sep. 2, 1993, abandoned.

[30] Foreign Application Priority Data

| Sep. 3, 1992 | [JP] | Japan | 4-260690 |
| Sep. 3, 1992 | [JP] | Japan | 4-260691 |

[51] Int. Cl.$^7$ .............. G01N 33/60; G03B 42/00
[52] U.S. Cl. ............................................. 250/583
[58] Field of Search ............................................. 250/583

[56] References Cited

U.S. PATENT DOCUMENTS

| 5,260,190 | 11/1993 | Shiraishi et al. | 435/6 |
| 5,347,139 | 9/1994 | Barker et al. | 250/583 |

FOREIGN PATENT DOCUMENTS

| 0159523 | 10/1985 | European Pat. Off. | 250/583 |
| 59-83058 | 5/1984 | Japan | 250/583 |
| 62-93679 | 4/1987 | Japan | 250/583 |

OTHER PUBLICATIONS

Grafton D. Chase and Joseph L. Rabinowitz, *Principles of Radioisotope Methodology*, Third Edition, Minneapolis, Minnesota, Burgess Publishing Company, 1967, pp. 171–173.

*Primary Examiner*—Constantine Hannaher
*Attorney, Agent, or Firm*—Sixbey, Friedman, Leedom & Ferguson, P.C.; Gerald J. Ferguson, Jr.; Jeffrey L. Costellia

[57] ABSTRACT

An autoradiographic process for obtaining locational information on two or more radioactively labeled substances which have different energy or half-life and are contained in a sample such as tissue of an organism. Specifically, the process includes the steps of placing the sample on a stimulable phosphor sheet having a plastic cover layer to cause the stimulable phosphor to absorb radiation energy of the labeled substances and reading the absorbed radiation energy out of the phosphor to obtain an image signal corresponding to one radioactively labeled substance and placing the sample on a stimulable phosphor sheet having a thinner plastic cover layer or no cover film to cause the stimulable phosphor to absorb radiation energy of the labeled substances and reading the absorbed radiation energy out of the phosphor to obtain image signals corresponding to plural radioactively labeled substances. Then, the process includes the step of subjecting the image signals of (a) and (b) to subtraction processing so that image signals corresponding to plural radioactively labeled substances can be separately obtained.

6 Claims, 1 Drawing Sheet

AUTORADIOGRAPHIC PROCESS

This application is a continuation of Ser. No. 08/667,283, filed Jun. 20, 1996, now abandoned; which is itself a continuation of Ser. No. 08/509,654, filed Jul. 31, 1995, now abandoned; which is a continuation of Ser. No. 08/353,339, filed Dec. 5, 1994, now abandoned; which is a continuation of Ser. No. 08/114,625, filed Sep. 2, 1993, now abandoned.

BACKGROUND OF THE INVENTION

1. Field of the Invention

This invention relates to an autoradiographic process. Particularly, the invention relates to an autoradiographic process for obtaining each locational information on at least two kinds of radioactively labeled substances which are contained in a sample selected from the group consisting of tissue of an organism and a medium containing tissue of an organism and/or substances originating from an organism.

2. Description of Prior Art

There has been heretofore known an autoradiographic process termed "autoradiography" or "radioautography" comprising the steps of: introducing a radioactively labeled substance into an organism; placing the organism or a part of tissue of the organism (i.e., a sample or specimen of animals, plants, fishes, etc.) on a radiographic film such as a high sensitivity type X-ray film for a given period of time to expose the film thereto; and obtaining the locational information on the radioactively labeled substance in the specimen from the resolved pattern of the film. The autoradiography has been utilized, for example, to investigate the pathway and state of metabolism, absorption, and excretion of the substance introduced into animals, plants, etc., in detail.

Recently, the autoradiography has been utilized for obtaining locational information on the radioactively labeled substances present on a medium containing radioactively labeled tissue of an organism or the radioactively labeled substances originating from an organism. For instance, there is known an autoradiography comprising the steps of: labeling organism-originating biopolymers such as proteins or nucleic acids with a radioactive element; resolving the mixture of the radioactively labeled biopolymers, derivatives thereof, or cleavage products thereof on a gel support (medium) through a resolving process such as gel electrophoresis: placing the gel support on a high sensitivity X-ray film for a given period of time to expose the film to the gel support, developing the film, obtaining the locational information of the radioactively labeled substances from the developed film, and then performing the identification of the polymeric substances, determination of molecular weight of the polymeric substances and isolation of the polymeric substances based on the obtained locational information.

Further, in order to anlalyze the pathway of an organism, an autoradiography utilizing the double-labeling method (i.e., double-tracer method) in which two kinds of radioactive isotopes are used has been proposed. The autoradiography comprises the steps of introducing each of radioactively labeled substances labeled with at least two kinds of radioactive isotopes different from each other into an organism and obtaining autoradiogram corresponding to each of the radioactively labeled substances (i.e., each isotope). Thus, this process is utilized to anlyze metabolism and chemical reaction in the organism.

As radiographic films employed for the autoradiography utilizing the double-labeling method, Japanese Patent Publication No. 47(1972)-45540 discloses a silver halide photographic photosensitive material for color autoradiography employable for distinguishably recording the distribution images of tritium ($^3H$) and other radioactive isotopes. The material comprises two silver halide emulsion layers each of which contains a coupler having hue different from each other and thicknesses of which are adjusted to enable the distinguishable recording.

In the autoradiography according to the conventional radiographic method, however, it is extremely difficult to obtain the autoradiogram corresponding to each isotope of a sample which is multiply labeled with different radioactive isotopes. Even if the radiographic film as mentioned above is employed for the multiply labeled sample, the resultant autoradiograms are visibly recorded on one radiographic film as color images having hues different from each other so that investigators are required to examine and analyze the each autoradiogram only by difference of the hues. Further, different autoradiograms are recorded on one radiographic film so that locational information on radioactively labeled substances can not accurately be obtained.

For this reason, a double-autoradiography (i.e., two nuclides labeled autoradiography) utilizing difference of half-lives of radioactive isotopes has been recently employed. This process comprises the steps of: introducing two kinds of radioactively labeled substances which are labeled with two nuclides having half-lives greatly different from each other (e.g., $^{123}I$: half-life of about 13 hours, $^{14}C$: half-life of about 5,730 years) into an organism; taking a sample from the organism after a certain period of time in order to examine distribution of each of the radioactively labeled substances in the organism; placing the sample on a radiographic film; immediately subjecting the film to autoradiography to obtain an image of the two kinds of radioactively labeled substances which are labeled with the two nuclides on the radiographic film; allowing the sample to stand for a long time (i.e., until the nuclide having a short half-life almost disappears); subjecting the sample to autoradiography similar to the above autoradiography to obtain an image of the radioactively labeled nuclide of a long half-life on the radiographic film; and performing a subtraction processing which comprises subtracting the latter image of the radioactively labeled substance obtained by autoradiography (i.e., an image showing distribution of the radioactively labeled nuclide of a long half-life in the sample) from the former image of the radioactively labeled substances obtained by the autoradiography to obtain an image showing distribution of the radioactively labeled nuclide of a short half-life in the sample.

In this process, although each of the images obtained above has high accuracy, a standing period required for allowing the nuclide having a short half-life to almost disappear is very long (e.g., in the combination of $^{123}I$ and $^{14}C$, about two months are required), which retards progress on the study. Further, since the relationship between the density of the image formed on the silver halide film (i.e., blackening image) and the radiation amount does not show simple linearity, the above subtraction processing is required to perform using a complicated formula of relation.

Further, such autoradiography using a radiographic film (i.e., silver halide photosensitive photographic film) is not free from several drawback in the practical use.

In order to obtain the autoradiogram, a procedure of placing a sample containing a radioactively labeled substances (which are labeled with radioactive isotopes) on a radiographic film such as a high-sensitivity X-ray film for a given period of time and exposing the film to the substances is performed. In this procesure, the exposing procedure requires a long period of time (ten hours to several days). This is because samples for the autoradiography generally do not have high radioactivity. Further, the exposing procedure must be performed at a low temperature (e.g., 0 to −80° C.). The reason is that a latent image of the photosensitive silver salt formed on the film is some-times faded to become an image which is not developable or that the latent image is chemically fogged by various substances harmful to silver salt which migrate from the sample into the film at relatively high temperatures. Such chemical fog results in difficulty of obtaining locational information on the radioactively labeled substances with high accuracy. Thus, the exposure ought to be carried out at a low temperature to reduce the chemical fog. Further, in order to prevent lowering of the image quality originating from the chemical fog, the example containing the radioactively labeled substances should be superposed on the radioactive film in the drying condition during the exposure, and therefore the example is generally required to be dried or to be packaged within a polymer film.

The photosensitive silver salt of a radiographic film has a drawback that it is further sensitive not only to the chemical irritation but also to physical impetus caused in such operation as transfer or setting of the film, this drawback brings about difficulty in the autoradiographic procedure and decreases accuracy thereof. In more detail, the radiographic film is likely brought into contact with samples, hands of the operator and tools in the handling, and such physical pressure arising from these contacts causes production of the physical fog on the radiographic film. The physical fog is also a cause of the decrease of accuracy in the autoradiography. For this reason, the handling of a radiographic film requires well-trained skill and great caution to avoid the production of the physical fog on the radiographic film, and such requirement of careful handling increases complexity in the autoradiographic procedure.

Further, certain natural radioactive substances contained in the sample in addition to the radioactively labeled substance take part in the exposure of the radiographic film because the exposure is carried out, as described above, for a long period of time in the conventional autoradiography. Thus, the influence of the natural radioactive substance further reduces the accuracy of locational information of the radioactively labeled substances, and this is an additional drawback. In order to remove the troublesome noise brought about by the natural radioactive substances, parallel experiments using control samples and a method for optimization of the exposure time have been employed, but these procedures include increased experimental runs for the parallel experiments and requires preliminary experiments to determine the preferable exposure time, and thus the drawback arising from the complicated procedures is not avoidable as whole.

In order to remove the drawbacks of the conventional autoradiography using the above photosensitive silver halide film, use of a stimulable phosphor sheet (i.e., radiation image storage panel) having a phosphor layer containing a stimulable phosphor as the photosensitive material has been already proposed in EP-A-0,111,154.

Further, to solve the problems observed in the autoradiography utilizing the double-labeling method, use of a stimulable phosphor sheet or a composite thereof having plural phosphor layers containing a stimulable phosphor as the photosensitive material has been already proposed in Japanese Patent Provisional Publication No. 62(1987)-93679.

Although the latter invention can effectively solve the above problems of the conventional autoradiography utilizing the double-labeling method, it is necessary to prepare plural stimulable phosphor layers (composite or plural stimulable phosphor sheets) having thicknesses different from each other, the number of the phosphor layers corresponding to the number of nuclides used. Further, the invention enables to obtain radiation images corresponding to plural nuclides by one read-out operation, while it is not easy to determine the conditions for separating these radiation images.

SUMMARY OF THE INVENTION

It is an object of the invention to provide an autoradiographic process in which the above-mentioned problems of the autoradiography utilizing the double-labeling method are solved, and particularly accurate radiation images sufficiently separated (i.e., influence of other radiation images can be neglected) having plural radioactively labeled substances (nuclides) are obtained by repeating a simple reading operation with no use of the plural stimulable phosphor layers and then preforming an operation of a simple signal processing.

There is provided by the present invention an autoradiographic process for obtaining locational information on at least two kinds of radioactively labeled substances which are labeled with radioactive isotopes having mean energies different from each other, said radioactively labeled substances being contained in a sample selected from the group consisting of tissue of an organism and a medium containing tissue of an organism or substances originating from an organism, which comprises:

(1) a step of placing said sample on a stimulable phosphor sheet comprising a phosphor layer and a protective layer thereon for a given period of time to cause the phosphor layer to absorb radiation energy emitted by the radioactively labeled substance having a higher mean energy;

(2) a step of obtaining an image signal showing locational information on the radioactively labeled substance having a higher mean energy, which comprises exciting the phosphor layer of the stimulable phosphor sheet with an electromagnetic wave to release the radiation energy stored in said phosphor layer as stimulated emission and detecting the stimulated emission;

(3) a step of placing said sample on a stimulable phosphor sheet comprising a phosphor layer on which no protective layer is provided or a thinner protective layer than the protective layer employed in the step (1), via the thinner or no protective layer, for a given period of time to cause said phosphor layer to absorb radiation energy emitted by both a radioactively labeled substance having a higher mean energy and one having a lower mean energy;

(4) a step of obtaining an image signal showing locational information of both the radioactively labeled substance having a higher mean energy and one having a lower mean energy, which comprises exciting said phosphor layer of said stimulable phosphor sheet having been subjected to the step (3) with an electromagnetic wave to release the radiation energy stored in the phosphor layer as stimulated emission and detecting the stimulated emission; and (5) a step of obtaining locational information on each of at least two kinds of radioactively labeled substances contained in said sample, which comprises subjecting the image signal obtained in the steps (2) and (4) to a subtraction processing for eliminating the image signal obtained in the step (2) from that obtained in the step (4).

There is further provided by the invention an autoradiographic process for obtaining locational information on at least two kinds of radioactively labeled substances which are labeled with radioactive isotopes having mean energies different from each other and a radioactively labeled substance which is labeled with a radioactive isotope having a half-life different from that of at least one of the former radioactive isotopes, all the radioactively labeled substances being contained in a sample selected from the group consisting of tissue of an organism and a medium containing tissue of an organism or substances originating from an organism, which comprises:

(I) a procedure for obtaining at least three image signals by performing at least three steps of the following four steps (1) to (4):

(1) a step of obtaining an image signal showing locational information on the radioactively labeled substance having a higher mean energy, which comprises placing the sample on a stimulable phosphor sheet comprising a phosphor layer and a protective layer thereon for a given period of time to cause the phosphor layer to absorb radiation energy emitted by the radioactively labeled substance having a higher mean energy, subsequently exciting the phosphor layer of the stimulable phosphor sheet with an electromagnetic wave to release the radiation energy stored in the phosphor layer as stimulated emission and detecting the stimulated emission;

(2) a step of obtaining an image signal showing locational information on both the radioactively labeled substance having a higher mean energy and one having a lower mean energy, which comprises placing the sample on a stimulable phosphor sheet comprising a phosphor layer on which no protective layer is provided or a thinner protective layer than the protective layer employed in the step (1) is provided, via the thinner or no protective layer, for a given period of time to cause the phosphor layer to absorb radiation energy emitted by both the radioactively labeled substance having a higher mean energy and one having a lower mean energy, subsequently exciting the phosphor layer of the stimulable phosphor sheet with an electromagnetic wave to release the radiation energy stored in the phosphor layer as stimulated emission and detecting the stimulated emission;

(3) a step of obtaining an image signal showing locational information on the radioactively labeled substance having a higher mean energy, which comprises allowing the sample to stand for a period determined on the basis of the shortest half-life of the radioactive isotope contained in the sample, thereafter placing the sample on a stimulable phosphor sheet comprising a phosphor layer and a protective layer thereon for a given period of time to cause the phosphor layer to absorb radiation energy emitted by the radioactively labeled substance having a higher mean energy, subsequently exciting the phosphor layer of the stimulable phosphor sheet with an electromagnetic wave to release the radiation energy stored in the phosphor layer as stimulated emission and detecting the stimulated emission; and (4) a step of obtaining an image signal showing locational information on both the radioactively labeled substance having a higher mean energy and one having a lower mean energy, which comprises allowing the sample to stand for a period determined on the basis of the shortest half-life of the radioactive isotope contained in the sample, thereafter placing the sample on a stimulable phosphor sheet comprising a phosphor layer on which no protective layer is provided or a thinner protective layer than the protective layer employed in the step (3) is provided, via the thinner or no protective layer, for a given period of time to cause the phosphor layer to absorb radiation energy emitted by both the radioactively labeled substance having a higher mean energy and one having a lower mean energy, subsequently exciting the phosphor layer of the stimulable phosphor sheet with an electromagnetic wave to release the radiation energy stored in the phosphor layer as stimulated emission and detecting the stimulated emission; and (II) a procedure of obtaining each of locational information on at least three kinds of radioactively labeled substances contained in the sample, which comprises subjecting the image signals obtained in the procedure (I) to a subtraction processing.

The autoradiographic process of the invention solves the above-mentioned problems of the autoradiography utilizing the double-labeling method, and particularly has an advantage that accurate radiation images sufficiently separated (i.e., influence of other radiation images can be neglected) having plural (preferably, of two or three kinds) radioactively labeled substances (nuclides) are obtained by repeating a simple reading operation without use of the plural stimulable phosphor layers and then performing an operation of a simple signal processing.

The autoradiographic process of the invention not only enables great reduction in exposure time but also causes no reduction of accuracy of the obtained locational information even if the exposure is carried out under temperature conditions such as an environmental temperature or the like. Accordingly, the exposure operation of the invention becomes extremely easy, in contrast to the fact that a conventional exposure operation is performed under chilling for a long time, and therefore the operation of the autoradiography according to the invention is greatly simplified.

Further, employment of the stimulable phosphor sheet as a photosensitive material for the autoradiographic process (i.e., autoradiography) substantially causes almost no production of chemical fog and physical fog which are great drawbacks in use of a radiation film, and such disappearance of the fog improves accuracy of the locational information and workability. Furthermore, reduction of accuracy of locational information caused by radioactivity of impurity contained in a sample or natural radioactivity is almost or perfectly removed by electrically processing locational information stored in a stimulable phosphor sheet.

DETAILED DESCRIPTION OF THE INVENTION

Figure 1:
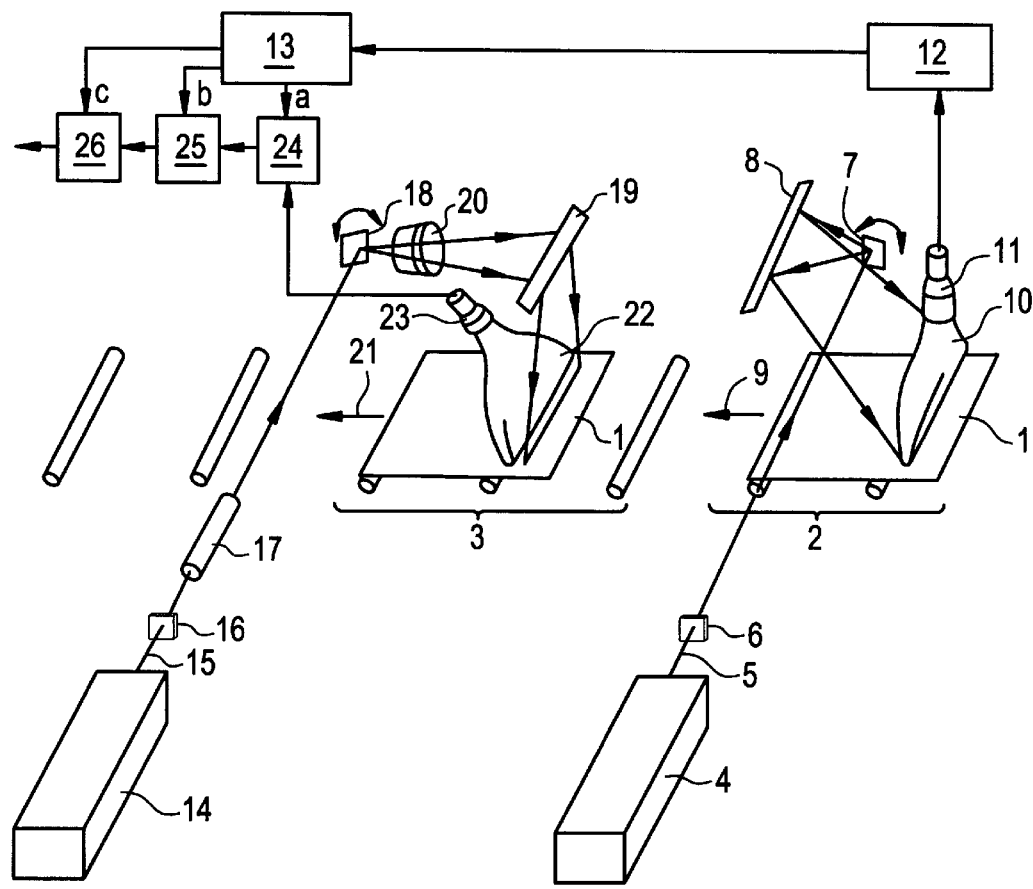
FIG. 1 shows an example of the read-out system for reading out the locational information on the radioactively labeled substance copied from the sample and stored in a stimulable phosphor sheet according to the invention.

The term "locational information" on the radioactively labeled substances contained in the sample in the present invention refers to various information such as the location of the radioactively labeled substance or its aggregate in the sample, for example, information on the location and the shape of the aggregate of the radioactively labeled substances in the sample and on the concentration, the distribution, etc. of the radioactively labeled substances or their aggregates. Such information can be obtained singly or in combination. Further, the term "at least two (or at least three) kinds of radioactively labeled substances" includes identical substances having different radioactive labels.

The stimulable phosphor sheet used in the invention is also called a radiation image storage panel and described in, for example, Japanese Provisional Publication No. 55(1980)-12145, etc. and thus its general constitution is already known.

The stimulable phosphor sheet comprises a stimulable phosphor, in which the stimulable phosphor is capable of absorbing radiation energy having passed through an object or radiated front an object; and releasing the radiation energy stored in the phosphor of the sheet as stimulated emission when the phosphor sheet is excited with an electromagnetic wave (i.e., stimulating rays) such as visible or infrared rays. The stimulated emission is photoelectrically detected and converted into electric signals which are then reproduced as a visible image on a display device such as a CRT or a recording medium such as a photographic film, or represented as a locational information in the form symbols and/or numerals.

The stimulable phosphor sheet has a basic structure comprising a support and a phosphor layer provided on one surface of the support. However, if the phosphor layer has self-supporting property, the sheet may not have the support. Further, a transparent protective film is generally provided on the free surface (surface not facing the support) of phosphor layer to keep the phosphor layer from chemical deterioration or physical shock.

The phosphor layer basically comprises a binder and stimulable phosphor particles dispersed therein.

The stimulable phosphor, as described hereinbefore, gives stimulated emission when excited by stimulating rays after exposure to a radiation. From the viewpoint of practical use, the stimulable phosphor is desired to give simulated emission in the wavelength region of 300–500 nm when excited by stimulating rays in wavelength region of 400–900 nm.

Examples of the stimulable phosphor employable in the stimulable phosphor sheet utilized in the invention include:

SrS:Ce, Sm, SrS:Eu, Sm, ThO$_2$:Er, and La$_2$O$_2$S:Eu, Sm, as described in U.S. Pat. No. 3,859,527;

ZnS:Cu, Pb, BaO·xAl$_2$O$_3$:Eu, in which x is a number satisfying the condition of $0.8 \leq x \leq 10$, and M$^{II}$O·xSiO$_2$:A, in which M$^{II}$ is at least one divalent metal selected from the group consisting of Mg, Ca, Sr, Zn, Cd or Ba, A is at least one element selected from the group consisting of Ce, Tb, Eu, Tm, Pb, Tl, Bi and Mn, and "x" is $0.5 \leq x \leq 2.5$, as described in Japanese Patent Provisional Publication No. 55(1980)-12142;

(Ba$_{1-x-y}$, Mg$_x$, Ca$_y$)FX:aEu$^{2+}$, in which X is at least one halogen selected from the group consisting of Cl and Br, "x" and "y" are numbers satisfying the conditions of $0<x+y \leq 0.6$ and $xy \neq 0$, and "a" is a number satisfying the condition of $1 \times 10^{-6} \leq a \leq 5 \times 10^{-2}$, as described in Japanese Patent Provisional Publication No. 55(1980)-12143;

LnOX:xA, in which Ln is at least one element selected from the group consisting of La, Y, Gd and Lu, X is at least one halogen selected from the group consisting of Cl and Br, A is at least one element selected from the group consisting of Ce and Tb, and "x" is a number satisfying the condition of $0<x<0.1$ as described in Japanese Patent Provisional Publication No. 55(1980)-12144;

(Ba$_{1-x}$, M$^{II}_x$)FX:yA, in which M$^{II}$ is at least one divalent metal selected from the group consisting of Mg, Ca, Sr, Zn and Cd, X is at least one halogen selected from the group consisting of Cl, Br and I, A is at least one element selected from the group consisting of Eu, Tb, Ce, Tm, Dy, Pr, Ho, Nd, Yb and Er, "x" is a number satisfying the condition of $0 \leq x \leq 0.6$ and "y" is a number satisfying the condition of $0 \leq y \leq 0.2$, as described in Japanese Patent Provisional Publication No. 55(1980)-12145;

M$^{II}$FX·xA:yLn, in which M$^{II}$ is at least one element selected from the group consisting of Ba, Ca, Sr, Mg, Zn and Cd, A is at least one element selected from the group consisting of BeO, MgO, CaO, SrO, BaO, ZnO, Al$_2$O$_3$, Y$_2$O$_3$, La$_2$O$_3$, In$_2$O$_3$, SiO$_2$, TiO$_2$, ZrO$_2$, GeO$_2$, SnO$_2$, Nb$_2$O$_5$, Ta$_2$O$_5$ and ThO$_2$, Ln is at least one element selected from the group consisting of Eu, Tb, Ce, Tm, Dy, Pr, Ho, Nd, Yb, Er, Sm and Gd, X is at least one halogen selected from the group consisting of Cl, Br and I, and "x" and "y" are numbers satisfying the conditions of $5 \times 10^{-5} \leq x \leq 0.5$ and $0<y \leq 0.2$, respectively, as described in Japanese Patent Provisional Publication No. 55(1980)-160078;

(Ba$_{1-x}$, M$^{II}_x$)F$_2$·aBaX$_2$:yEu, zA, in which M$^{II}$ is at least one divalent metal selected from the group consisting of Be, Mg, Ca, Sr, Zn and Cd, X is at least one halogen selected from the group consisting of Cl, Br and I, A is at least one element selected from the group consisting of Zr and Sc, and "a", "x", "y" and "z" are numbers satisfying the conditions of $0.5 \leq a \leq 1.25$, $0 \leq x \leq 1$, $1 \times 10^{-6} \leq y \leq 2 \times 10^{-1}$ and $0<z \leq 1 \times 10^{-2}$, respectively, as described in Japanese Patent Provisional Publication No. 56(1981)-116777;

(Ba$_{1-x}$, M$^{II}_x$)F$_2$·aBaX$_2$:yEu,zB, in which M$^{II}$ is at least one divalent metal selected from the group consisting of Be, Mg, Ca, Sr, Zn and Cd, X is at least one halogen selected from the group consisting of Cl, Br and I, and "a", "x", "y" and "z" are numbers satisfying the conditions of $0.5 \leq a \leq 1.25$, $0 \leq x \leq 1$, $1 \times 10^{-6} \leq y \leq 2 \times 10^{-1}$ and $0<z \leq 2 \times 10^{-1}$, as described in Japanese Patent Provisional Publication No. 57(1982)-23673;

(Ba$_{1-x}$, M$^{II}_x$)F$_2$·aBaX$_2$:yEu,zA, in which M$^{II}$ is at least one divalent metal selected from the group consisting of Be, Mg, Ca, Sr, Zn and Cd, X is at least one halogen selected from the group consisting of Cl, Br and I, A is at least one element selected from the group consisting of As and Si, and "a", "x", "y" and "z" are numbers satisfying the conditions of $0.5 \leq a \leq 1.25$, $0 \leq x \leq 1$, $1 \times 10^{-6} \leq y \leq 2 \times 10^{-1}$ and $0<z \leq 5 \times 10^{-1}$, respectively, as described in Japanese Patent Provisional Publication No. 57(1982)-23675;

M$^{III}$OX:xCe, in which M$^{III}$ is at least one trivalent metal selected from the group consisting of Pr, Nd, Pm, Sm, Eu, Tb, Dy, Ho, Er, Tm, Yb and Bi, X is at least one halogen selected from the group consisting of Cl and Br, and "x" is a number satisfying the condition of $0<x<0.1$, as described in Japanese Patent Provisional Publication No. 58(1983)-69281;

Ba$_{1-x}$M$_{x/2}$L$_{x/2}$FX:yEu$^{2+}$, in which M is at least one alkali metal selected from the group consisting of Li, Na, K, Rb and Cs, L is at least one trivalent metal selected from the group consisting of Sc, Y, La, Ce, Pr, Nd, Pm, Sm, Gd, Tb, Dy, Ho, Er, Tm, Yb, Lu, Al, Ga, In and Tl, X is at least one halogen selected from the group consisting of Cl, Br and I, and "x" and "y" are numbers satisfying the conditions of $1 \times 10^{-2} \leq x \leq 0.5$ and $0<y \leq 0.1$, respectively, as described in Japanese Patent Provisional Publication No. 58(1983)-206678;

BaFX·xA:yEu$^{2+}$, in which X is at least one halogen selected from the group consisting of Cl, Br and I, A is at least one fired product of a tetrafluoroboric acid compound and "x" and "y" are numbers satisfying the conditions of $1\times10^{-6} \leq x \leq 0.1$ and $0<y \leq 0.1$, respectively, as stated in Japanese Patent Provisional Publication No. 59(1984)-27980;

BaFX·xA:yEu$^{2+}$, in which X is at least one halogen selected from the group consisting of Cl, Br and I, A is at least one fired product of a hexafluoro compound selected from the group consisting of monovalent and divalent metal salts of hexafluoro silicic acid, hexafluoro titanic acid and hexafluoro zirconic acid, and "x" and "y" are numbers satisfying the conditions of $1\times10^{-6} \leq x \leq 0.1$ and $0<y \leq 0.1$, respectively, as described in Japanese Patent Provisional Publication No. 59(1984)-47289;

BaFX·xNaX':aEu$^{2+}$, in which each of X and X' is at least one halogen selected from the group consisting of Cl, Br and I, A is at least one element selected from the group consisting of As and Si, and "x" and "a" are number satisfying the conditions of $0<x \leq 2$ and $0<a \leq 0.2$, respectively, as described in Japanese Patent Provisional Publication No. 59(1984)-56479;

M$^{II}$FX·xNaX':yEu$^{2+}$:zA, in which M$^{II}$ is at least one alkaline earth metal selected from the group consisting of Ba, Sr and Ca, each of X and X' is at least one halogen selected from the group consisting of Cl, Br and I, A is at least one element selected from the group consisting of V, Cr, Mn, Fe, Co and Ni, and "x", "y" and "z" are numbers satisfying the conditions of $0<x \leq 2$, $0<y \leq 0.2$ and $0<z \leq 1\times10^{-2}$, respectively, as described in Japanese Patent Provisional Publication No. 59(1984)-56480;

M$^{II}$FX·aM$^{I}$X'·bM$^{II}$X''$_2$·cM$^{III}$X'''$_3$·xA:yEu$^{2+}$:zA, in which M$^{II}$ is at least one alkaline earth metal selected from the group consisting of Ba, Sr and Ca, M$^{I}$ is at least one alkali metal selected from the group consisting of Na, K, Rb and Cs, M$^{II}$ is at least one divalent metal selected from the group consisting of Be and Mg, Mg$^{III}$ is at least one trivalent metal selected from the group consisting of Al, Ga, In and Tl, A is a metal oxide, X is at least one halogen selected from the group consisting of Cl, Br and I, X', X" and X'" each are at least one halogen selected from the group consisting of F, Cl, Br and I, and "a", "b" and "c" are numbers satisfying the conditions of $0 \leq a \leq 2$, $0<b \leq 1\times10^{-2}$, $0 \leq c \leq 1\times10^{-2}$ and $a+b+c \geq 1\times10^{-6}$, and "x" and "y" are numbers satisfying the conditions of $0<x \leq 0.5$ and $0<y \leq 0.2$, respectively, as described in Japanese Patent Provisional Publication No. 59(1984)-75200;

M$^{II}$X$_2$·aM$^{II}$X'$_2$:xEu$^{2+}$, in which M$^{II}$ is at least one alkaline earth metal selected from the group consisting of Ba, Sr and Ca, X and X'0 each are at least one halogen selected from the group consisting of Cl, Br and I and are halogens satisfying the condition of X≠X', and "a" and "x" are numbers satisfying the conditions of $0.1 \leq a \leq 10$ and $0<x \leq 2$, respectively, as described in Japanese Patent Provisional Publication No. 60(1985)-84381;

M$^{II}$FX·aM$^{I}$X':xEu$^{2+}$, in which M$^{II}$ is at least one alkaline earth metal selected from the group consisting of Ba, Sr and Ca, M$^{I}$ is at least one alkali metal selected from the group consisting of Rb and Cs, X is at least one halogen selected from the group consisting of Cl, Br and I, X' is at least one halogen selected from the group consisting of F, Cl, Br and I, and "a" and "x" are numbers satisfying the conditions of $0 \leq a \leq 4.0$ and $0<x \leq 0.2$, respectively, as described in Japanese Patent Provisional Publication No. 60(1985)-101173;

M$^{I}$X:xBi, in which M$^{I}$ is at least one alkali metal selected from the group consisting of Rb and Cs, X is at least one halogen selected from the group consisting of Cl, Br and I, and "x" is a number satisfying the condition of $0<x \leq 0.2$, as described in Japanese Patent Provisional Publication No. 62(1985)-25189; and LnOX:xCe, in which Ln is at least one trivalent metal selected from the group consisting of La, Y, Gd and Lu, X is at least one halogen selected from the group consisting of Cl, Br and I, "x" is a number satisfying the condition of $0 \leq x \leq 0.1$, the ratio of Ln and X is a value satisfying the condition of $0.500<X/Ln \leq 0.998$ at atomic ratio, and the maximum of the stimulable emission spectrum ($\lambda$) is wavelength satisfying the condition of 550 nm$<\lambda<$700 nm, as described in Japanese Patent Provisional Publication No. 2(1990)-229882.

M$^{II}$X$_2$·aM$^{II}$X'$_2$:xEu$^{2+}$ in Japanese Patent Provisional Publication No. 60(1985)-84381 as mentioned above may contain the following additives in the following amount per M$^{II}$X$_2$·aM$^{II}$X'$_2$ of 1 mole:

bM$^{I}$X" in which M$^{I}$ is at least one alkali metal selected from the group consisting of Rb and Cs, X is at least one halogen selected from the group consisting of F, Cl, Br and I, "b" is a number satisfying the condition of $0<b \leq 10.0$, as described in Japanese Patent Provisional Publication No. 60(1985)-166379; bKX"·cMg X'"$_2$·dM$^{III}$ X""$_3$ in which M$^{III}$ is at least one trivalent metal selected from the group consisting of Sc, Y, La, Gd and Lu, X", X'" and X"" are at least one halogen selected from the group consisting of F, Cl, Br and I, and "b", "c" and "d" are numbers satisfying the conditions of $0 \leq b \leq 2.0$, $0 \leq c \leq 2.0$, $0 \leq d \leq 2.0$ and b+c+d$\geq 2\times10^{-5}$, as described in Japanese Patent Provisional Publication No. 60(1985)-221483; yB in which "y" is a number satisfying the condition of $2\times10^{-4} \leq y \leq 2\times10^{-1}$, as described in Japanese Patent Provisional Publication No. 60(1985)-228592; bA in which A is at least one oxide selected from the group consisting of SiO$_2$ and P$_2$O$_5$, and "b" is a number satisfying the condition of $1\times10^{-4} \leq b \leq 2\times10^{-1}$, as described in Japanese Patent Provisional Publication No. 60(1985)-228593; bSiO in which "b" is a number satisfying the condition of $0<b \leq 3\times10^{-2}$, as described in Japanese Patent Provisional Publication No. 61(1986)-120883; bSnX"$_2$ in which X" is at least one halogen selected from the group consisting of F, Cl, Br and I, and "b" is a number satisfying the condition of $0<b \leq 1\times10^{-3}$, as described in Japanese Patent Provisional Publication No. 61(1986)-120885; bCsX"·cSnX'"$_2$ in which X" and X'" each are at least one halogen selected from the group consisting of F, Cl, Br and I, and "b" and "c" are numbers satisfying the conditions of $0<b \leq 10.0$ and $1\times10^{-6}<c \leq 2\times10^{-2}$, respectively, as described in Japanese Patent Provisional Publication No. 61(1986)-235486; and bCsX"·yLn$^{3+}$ in which X" is at least one halogen selected from the group consisting of F, Cl, Br and I, Ln is at least one rare earth element selected from the group consisting of Sc, Y, Ce, Pr, Nd, Sm, Gd, Tb, Dy, Ho, Er, Tm, Yb and Lu, and "b" and "y" are numbers satisfying the conditions of $0<b \leq 10.0$ and $1\times10^{-6}<y \leq 1.8\times10^{-1}$, respectively, as described in Japanese Patent Provisional Publication No. 61(1986)-235487.

The above-described stimulable phosphors are given by no means to restrict the stimulable phosphor employable in the invention. Any other phosphors can be also employed, provided that the phosphors give stimulated emission when excited with stimulating rays after exposure to radiation. Preferred stimulable phosphors in the invention include divalent europium activated alkaline earth metal halide phosphor and cerium activated rare earth element oxyhalide phosphor which show stimulated emission of high luminance.

The phosphor layer of the stimulable phosphor sheet of the invention generally comprises the stimulable phosphor and a binder in which the phosphor is dispersed. However, the phosphor layer may be merely composed of an agglomerated stimulable phosphor containing no binder, or may be composed of an agglomerated stimulable phosphor and a polymer impregnated into voids of the agglomerated phosphor.

Subsequently, the process for the preparation of the stimulable phosphor sheet of the invention is described hereinafter.

A process for the preparation of the stimulable phosphor sheet of the invention is described below referring to a stimulable phosphor sheet comprising a support and a phosphor layer provided thereon which comprises a binder and a stimulable phosphor dispersed therein.

The phosphor layer can be provided on the support, for example, by the following known process.

The stimulable phosphor and a binder (e.g., nitrocellulose, acrylic resin or thermoplastic elastomer) are added to an appropriate solvent, and they are well mixed to prepare a coating dispersion for the formation of a phosphor layer in which the stimulable phosphor particles are uniformly dispersed in a binder solution. A ratio between the binder and the phosphor in the coating dispersion may be determined according to the characteristics of the aimed stimulable phosphor sheet and the nature of the phosphor employed. Generally, the ratio therebetween is in the range of 1:1 to 1:100 (binder:phosphor, by weight), preferably 1:8 to 1:40.

The coating dispersion containing the phosphor particles and the binder prepared as above is applied evenly to the surface of a support to form a layer of the coating dispersion. The coating procedure can be carried out by a conventional method such as a method of using a doctor blade, a roll coater or a knife coater.

A support material employable in the invention can be selected from those employed in the conventional stimulable phosphor sheets. In the preparation of a known stimulable phosphor sheet, one or more additional layers are occasionally provided between the support and the phosphor layer, so as to enhance the adhesion between the support and the phosphor layer, or to improve the sensitivity of the sheet or the quality of an image (sharpness and graininess). For example, an adhesive layer or subbing layer may be provided by coating a polymer material such as gelatin over the surface of the support on the phosphor layer side. Otherwise, a light-reflecting layer or a light-absorbing layer may be provide by forming a polymer material layer containing a light-reflecting material such as titanium dioxide or a light-absorbing material such as carbon black. One or more of these additional layers may be provided on the support, and the constitution thereof can be optionally selected depending upon the purpose of the stimulable phosphor sheet.

The phosphor layer-side surface of the support (or the surface of an adhesive layer, a light-reflecting layer, or light-absorbing layer in the case that such layers are provided on the phosphor layer) may be provided with protruded and depressed portions for enhancement of the sharpness of a radiation image.

The coating dispersion is coated over the support as described above. Then the coated layer of the dispersion is dried to complete formation of a stimulable phosphor layer on the support. The thickness of the phosphor layer varies depending upon the characteristics of the aimed stimulable phosphor sheet, the nature of the phosphor, the ratio between the binder and the phosphor, etc. Generally, the thickness of the phosphor layer is in the range of 20 $\mu$m to 1 mm, preferably in the range of 50 to 500 $\mu$m.

The stimulable phosphor sheet of the invention has generally a protective film on a free surface of the phosphor layer. The protective film can be provided on the phosphor layer by evenly coating the surface of the phosphor layer, using a doctor blade or the like, with a solution which is prepared by dissolving a transparent polymer material such as a cellulose derivative (e.g., cellulose acetate or nitrocellulose) or a synthetic polymer (e.g., polymethyl methacrylate, polyvinyl butyral, polyvinyl formal, polycarbonate, polyvinyl acetate or vinyl chloride. vinyl acetate copolymer) in an appropriate solvent, and drying the coated solution. Alternatively, the protective film can be provided on the phosphor layer by beforehand preparing a protective film from a plastic sheet of polyethylene terephthalate, polyethylene naphthalate, polyethylene, polyvinylidene chloride or polyamide or a transparent glass sheet, followed by placing and fixing it onto the phosphor layer with an appropriate adhesive agent. Otherwise, the protective film can be also provided by depositing an inorganic compound on the phosphor layer. Further, the protective layer may be a coating film formed by using a fluoro-resin capable of being dissolved in an organic solvent, in which perfluoroolefin resin powders or silicon resin powders are dispersed.

The thickness of the protective layer of the stimulable phosphor sheet is appropriately determined depending on the kind, the content, or the released radiation strength of the radioactive isotope contained in the sample. In more detail, the distribution of the radioactively labeled substances labeled with a relatively high radiation energy in the sample is determined using a stimulable phosphor sheet provided with a thick protective layer, while the distribution of the radioactively labeled substances labeled with a relatively low radiation energy in the sample is determined using a stimulable phosphor sheet provided with a thin protective layer or no protective layer.

Examples of radioactive isotopes for imparting radioactive label into the example include $^3$H (mean energy: 0.0055 MeV; half-life: 12.3 years), $^{123}$I ($\gamma$-rays; mean energy: 0.159 MeV; half-life: 13 hours), $^{131}$I (mean energy: 0.004 MeV; half-life: 8 days), $^{14}$C (mean energy: 0.049 MeV; half-life: 5,730 years), $^{35}$S (mean energy: 0.048 MeV; half-life: 87 days), $^{32}$P (mean energy: 0.0695 MeV; half-life: 14.28 days) and $^{18}$F (mean energy: 0.64 MeV; half-life: 110 minutes).

For example, in the case that a sample contains $^3$H and $^{14}$C, the radiation of a relative low mean energy emitted by a radioactive isotope ($^3$H) is absorbed by a phosphor layer of a stimulable phosphor by placing the sample on the phosphor layer with intermediate layer (e.g., protective layer) as described above. In this case, the radiation of a relative high mean energy emitted by a radioactive isotope ($^{14}$C) is also absorbed by the phosphor layer at the same time. In the above procedure, both an image of the $^3$H-labeled substance and that of the $^{14}$C-labeled substance are simultaneously stored (or recorded) in the stimulable phosphor sheet.

Therefore, in the case of placing the sample on the phosphor layer via a protective layer having an appropriate thickness (e.g., 5–50 μm), the radiation emitted by a radioactive isotope ($^{14}C$) passes through the protective layer due to its high mean energy and is absorbed by the phosphor layer, while the radiation emitted by a radioactive isotope ($^3H$) can not pass through the protective layer. Accordingly, only an image of the $^{14}C$-labeled substance is absorbed by the phosphor layer.

By subtracting the radiation image having only the radiation image having the image of the $^{14}C$-labeled substance from the radiation image having both the image of the $^3H$-labeled substance and that of the $^{14}C$-labeled substance, a radiation image having only the image of the $^3H$-labeled substance can be obtained. Thus, an independent radiation image having the image of the $^3H$-labeled substance and an independent radiation image having the image of the $^{14}C$-labeled substance can be obtained, respectively.

In the above procedures, there are no specific limitations with respect to the order of the exposing procedures. Further, the exposing procedure and the read-out operation of locational information on the radioactive labeled substance (which is absorbed by the stimulable phosphor sheet) may be continuously performed, or the readout operation may be collectively performed after completion of all the exposure operations. Thus, the order of performing the operations is not restricted.

Similarly, in the case that an sample contains three kinds of radioactively labeled substances which are labeled with three kinds of radioactive isotopes ($^3H$, $^{14}C$ and $^{32}P$), the radiation of a relative low mean energy emitted by a radioactive isotope ($^3H$) is absorbed by a phosphor layer of a stimulable phosphor by placing the sample on the phosphor layer with no protective layer. In this case, radiations of a higher mean energy emitted by two kinds of radioactive isotopes ($^{14}C$ and $^{32}P$) are also absorbed by the phosphor layer at the same time. Accordingly, an image of the $^3H$-labeled substance, that of the $^{14}C$-labeled substance and that of the $^{32}S$-labeled substance are stored (or recorded) in the stimulable phosphor sheet.

The radiations emitted by radioactive isotopes ($^{14}C$ and $^{32}P$) have a high mean energy. In the case of placing the sample on a phosphor layer through a protective layer having a thickness of 5–50 μm, these radiations pass through the protective layer and are absorbed by the phosphor layer, while the radiation emitted by a radioactive isotope ($^3H$) cannot pass through the protective layer. Accordingly, an image of the $^{14}C$-labeled substance and the $^{32}P$-labeled substance are recorded on the phosphor layer of the stimulable phosphor sheet.

The radiations emitted by a radioactive isotope ($^{32}P$) have a high transmission power (a high mean energy). In the case of placing the sample on a phosphor layer through a protective layer having a thickness of about 100 μm, theses radiations pass through the protective layer and are absorbed by the phosphor layer, while the radiations emitted by radioactive isotopes ($^3H$ and $^{14}C$) can not pass through the protective layer. Accordingly, only the image of the $^{32}P$-labeled substance is recorded on the phosphor layer.

By processing the first radiation image having all of the images of the $^3H$-labeled substance, the $^{14}C$-labeled substance and $^{32}S$-labeled substance, the second radiation image having both of the images of the $^{14}C$-labeled substance and the $^{32}S$-labeled substance, and the final radiation image having the image of the $^{32}S$-labeled substance for subtraction, an independent radiation image having the image of the $^3H$-labeled substance, an independent radiation image having the image of $^{14}C$-labeled substance and an independent radiation image having the image of the $^{32}S$-labeled substance can be obtained, separately.

Hence, appropriate combination of the kind of the radioactive isotopes and the thickness of the protective layer (or no use of protective layer) as described above makes each of distributions (locational information) of at least two kinds of radioactively labeled substances obtainable.

Subsequently, the procedures for obtaining locational information of at least three kinds of radioactively labeled substances utilizing difference of half-life of the radioactive isotope of the radioactively labeled substance are explained below.

The explanation is made referring to the case that an sample contains $^3H$, $^{14}C$, and $^{123}I$. The radioactive isotope ($^3H$) generates radiation of a relative low mean energy which is absorbed a phosphor layer of a stimulable phosphor by placing the sample on the phosphor layer with no protective layer. In this case, the radiations of a higher mean energy emitted by radioactive isotopes ($^{14}C$ and $^{123}I$) are also absorbed by the phosphor layer at the same time. In the above procedure, three kinds of radiation images, namely an image of the $^3H$-labeled substance, that of the $^{14}C$-labeled substance and that of the $^{123}I$-labeled substance are simultaneously stored (recorded) in the stimulable phosphor sheet.

In the case of placing the sample on the phosphor layer via a protective layer having an appropriate thickness (e.g., 5–50 μm), the radiations of a high mean energy emitted by radioactive isotopes ($^{14}C$ and $^{123}I$) pass through the protective layer and are absorbed by the phosphor layer, while the radiation emitted by the radioactive isotope ($^3H$) cannot pass through the protective layer. Accordingly, an image of $^{14}C$-labeled substance and that of $^{123}I$-labeled substance are recorded on the phosphor layer of the stimulable phosphor sheet.

Further, when the radioactive isotope ($^{123}I$) having a short half-life in the above sample almost disappears after allowing it to stand for a period of two months, the sample is subjected to a procedure similar to the above procedure.

At this time, the radiation emitted by the radioactive isotope ($^3H$) of a lower mean energy is absorbed by the phosphor layer of the stimulable phosphor by placing the sample on the phosphor layer with no protective layer. In this case, a radioactive isotope which generates radiation of a higher mean energy is only $^{14}C$, and therefore only the radiation emitted by the radioactive isotope $^{14}C$ is also absorbed by the phosphor layer at the same time. In more detail, two kinds of radiation images of an image of $^3H$-labeled substance and that of $^{14}C$-labeled substance are simultaneously recorded on the stimulable phosphor sheet.

In the case of placing the sample on the phosphor layer via a protective layer having an appropriate thickness (e.g., 5–50 μm), the radiation emitted by the radioactive isotope ($^{14}C$) passes through the protective layer and is absorbed by the phosphor layer, while radiation emitted by the radioactive isotope ($^3H$) cannot pass through the protective layer. Accordingly, an image of $^{14}C$-labeled substance only is recorded on the stimulable phosphor sheet.

The radiation images obtained in the above processes are summarized below.

|  | Immediately after preparation of sample | | After standing of two months | |
| --- | --- | --- | --- | --- |
|  | Protective layer | No protective layer | Protective layer | No protective layer |
| $^3$H | None | Observed | None | Observed |
| $^{14}$C | Observed | Observed | Observed | Observed |
| $^{123}$I | Observed | Observed | None | None |

By subtracting the radiation image obtained by the procedure utilizing a protective layer after standing of two months from the radiation image obtained by the procedure utlizing no protective layer after standing of two months, a separate image of $^3$H-labeled substance is given as an independent radioactive image. Otherwise, the independent radioactive image is obtained by subtracting the radiation image obtained by the operation utilizing a protective layer immediately after preparation of the sample from a radiation image obtained by the operation utilizing no protective layer immediately after preparation of the sample.

Further, a radiation image obtained by the operation utilizing a protective layer after standing of two months is an independent radiation image of $^{14}$C-labeled substance.

Furthermore, a separate image of $^{123}$I-labeled substance is obtained as an independent radioactive image by subtracting the radiation image obtained by the operation utilizing no protective layer after standing of two months from the radiation image obtained by the operation utilizing no protective layer immediately after preparation of the sample. Otherwise, an independent radiation image is obtained by subtracting the radiation image obtained by the operation utilizing a protective layer after standing of two months from the radiation image obtained by the operation using a protective layer immediately after preparation of the sample. Hence, each of images of $^3$H-labeled substance, the $^{14}$C-labeled substance and $^{123}$I-labeled substance can be obtained as an independent radiation image.

In the above process, four exposing procedures of autoradiography are performed in total, whereas it is apparent that each of images of $^3$H-labeled substance, $^{14}$C-labeled substance and $^{123}$I-labeled substance desired can be obtained as a radiation image even when one of the four exposure operations is omitted (e.g., the exposing procedure utilizing a protective layer immediately after preparation of the sample, that utilizing no protective layer immediately after preparation of the sample or that utilizing no protective layer after standing of two months). Further, it is also possible that the exposure operation utilizing a protective layer after standing of two months is omitted. In this case, an independent image of $^{14}$C-labeled substance can be obtained by steps of obtaining each of images of $^3$H-labeled substance and $^{123}$I-labeled substance by the above process, and then subtracting both the images from a image obtained by the procedure utilizing no protective layer immediately after preparation of the sample.

In more detail, by appropriately choosing the natures of the radioactive isotopes and the thickness of the protective layer (or no use of protective layer) and to appropriately postpone the exposure in considerate of difference of half-lives of used radioactive isotopes, distributions (locational information) of at least three kinds of radioactively labeled substances can be independently obtained.

In the above process, there are no specific limitations with respect to the order of the exposing procedures (placing the sample on the stimulable phosphor sheet). Further, the exposing procedure and the read-out operation of locational information on the radioactive labeled substance (which is absorbed by the stimulable phosphor sheet) may be continuously performed, or the read-out operation may be collectively performed after completion of all the exposing procedures. Thus, the order or the time of performing the procedures and operations is not restricted.

Subsequently, the autoradiographic process (i.e., autoradiography) of the invention is described below.

The autoradiographic process of the invention employs the above stimulable phosphor sheet instead of the conventional radiographic film, and its exposure operation comprises placing the sample containing radioactively labeled substances on the stimulable phosphor sheet for a given period of time to allow at least a portion of radiation emitted by the radioactively labeled substances to be absorbed by the sheet.

The sample to be processed by the autoradiography of the invention is a sample selected from the group consisting of tissue of an organism (e.g., animals, plants, fish, or the like) and a medium containing tissue of an organism and/or substances originating from an organism. Examples of the medium containing tissue of an organism and/or substances originating from an organism include developed media of biopolymers such as proteins and nucleic acids, derivative thereof and cleavage products thereof.

The radioactively labeled substance contained the above sample is obtainable by introducing radioactive isotopes into the sample or the specific substance in the sample according to the known method The radioactive isotopes employed in the invention may be any nuclides which emit radiations (e.g., α-rays, β-rays, γ-rays, neutron, X-rays, etc.). Representative examples include $^3$H, $^{123}$I, $^{131}$I, $^{14}$C, $^{35}$S, $^{18}$F, and $^{32}$P. The sample to be processed by the invention contains at least two kinds of radioactively labeled substances which are labeled with radioactive isotopes having mean energies different from each other. In other example, the sample to be recorded of the invention contains at least three kinds of radioactively labeled substances of at least two kinds of radioactively labeled substances which are labeled with radioactive isotopes having mean energies different from each other and a radioactively labeled substance which is labeled with a radioactive isotope having half-life different from that of at least one of said radioactive isotopes (generally having a short half-life). Further, the radioactively labeled substances are distributed in two-dimensions in the sample.

In the exposing procedure, the sample is, optionally after being subjected to optional treatments such as drying treatment and fixing treatment of separately developing product, placed on the stimulable phosphor sheet, whereby the autoradiogram of the sample is recorded on the stimulable phosphor sheet. In this procedure, the sample may be placed under the stimulable phosphor sheet.

The exposing procedure in the condition of placing the sample on the sheet (exposing procedure in layers) is generally performed twice using two stimulable phosphor sheets differing in the protective layer. For example, a process which comprises using two stimulable phosphor sheets which are the same sheets except that one has a protective layer while the other has no protective layer (or has a thin protective layer) and performing exposing procedure in the condition of placing the sample on each of the sheet separately, is utilized. In another example, a process which comprises the steps of once performing the exposing procedure using a stimulable phosphor sheet having a protective layer, subsequently performing read-out operation of the radiation image, further removing radiation remaining in the stimulable phosphor sheet by means of erasing operation, and then performing the exposing procedure and readout operation in the same manner as above after removal of the protective layer from the erased stimulable phosphor sheet, is also utilized. Further, a process which comprises performing the exposing procedure using a stimulable phosphor sheet having a phosphor layer and a protective layer and having no support at the side having no protective layer, subsequently performing read-out operation of the radiation image, further removing radiation energy remaining in the stimulable phosphor sheet by means of erasing operation, and then performing the exposure and read-out operation at the side of the protective layer, is also utilized. Furthermore, a process which comprises performing operation of the exposure using a stimulable phosphor sheet having a support, a phosphor layer and a protective layer on the side of the protective layer, subsequently performing read-out operation of the radiation image, further removing radiation energy remaining in the stimulable phosphor sheet by means of an erasing operation, and then performing the exposing procedure and read-out operation on the side of the support, is also utilized.

It is desirable that each of the stimulable phosphor sheet employed above has the same except that the protective layer is varied in order to simplify the subtracting processing which is performed later. However, even if each of the stimulable phosphor sheet has the same construction as above, the substraction processing can be performed by introducing variables depending on materials of the phosphor layer and difference of the thickness of a layer into the substraction processing.

The exposure is performed for a given period of time such as several seconds or more, although the exposure period varies depending on the kind of radioactive isotopes contained in the sample, their radiation strengths, concentration and density of radioactively labeled substances, sensitivity of the stimulable phosphor sheet and locational relationship of the sample and the stimulable phosphor sheet. However, the exposure time in the case of using the stimulable phosphor sheet according to the invention is greatly reduced, as compared with that in the case of using the conventional radiation film.

The temperature for performing the exposing procedure is particularly restricted. In the autoradiography using the stimulable phosphor sheet of the invention, the exposing procedure can be performed at an environmental temperature (e.g., 10–35° C.). Further, the exposing procedure may be performed at a low temperature (e.g., about 5° C. or less) which is adopted in the conventional autoradiography.

An exposing procedure after allowing the sample to stand for a given period is also performed in the same manner as above.

A method for reading out or detecting the locational information on the radioactively labeled substances showm on the autoradiogram stored in the stimulable phosphor sheet is described below briefly, referring to an embodiment of a read-out system in FIG. 1.

FIG. 1 schematically illustrates an embodiment of the read-out system comprising a preliminary read-out section 2 for preliminarily reading out the one- or two-dimensional information on the location of the radioactively labeled substances stored (or recorded) in the stimulable phosphor sheet 1 (stimulable phosphor sheet may be hereinafter referred to as "phosphor sheet"), and a final read-out section 3 for finally reading out the desired locational information on the the radioactively labeled substances shown by the autoradiogram stored in the phosphor sheet 1.

In the preliminary read-out section 2, the preliminary read-out operation is carried out in the following manner.

Laser beam 5 generated by a laser source 4 first passes through a filter 6 to cut off a light beam in the wavelength region corresponding to the wavelength region of stimulated emission to be emitted from the phosphor sheet 1 in response to stimulation with the laser beam 5. The laser beam 5 is subsequently deflected by a beam deflector 7 such as a galvanometer mirror, and reflected by a plane reflecting mirror 8. The deflected beam then impinges upon the phosphor sheet 1. The laser source 4 used herein is so selected as to avoid overlapping of the wavelength region of the laser beam 5 with the main wavelength region of the stimulated emission to be emitted by the phosphor sheet 1.

The phosphor sheet 1 is transferred in the direction along the arrow 9 under the irradiation of the above-mentioned deflected laser beam. Therefore, the whole surface of the phosphor sheet 1 is subjected to the radiation of the deflected laser beam. The power of the laser beam 5 employed in the preliminary read-out section is adjusted to be lower than the power of the laser beam to be employed in the final read-out section by controlling the output of the laser source 4, the beam diameter of the laser beam 5, the scanning speed of the laser beam 5, and the transferring speed of the phosphor sheet 1.

When irradiated with the above-mentioned laser beam, the phosphor sheet 1 gives stimulated emission having the emission intensity proportional to the radiation energy stored (or recorded) therein. The emission then enters into a light guiding sheet 10 for the preliminary read-out. The light guiding sheet 10 has a linear edge face for receiving the emission, and the edge face is so positioned in the vicinity of the phosphor sheet as to correspond to the scanning line on the phosphor sheet 1. The exit of the light guiding sheet 10 is in the form of a ring and is connected to an light-receiving face of a light detector 11 such as a photomultiplier. The light guiding sheet 10 is made, for instance, by processing a sheet of a transparent thermoplastic resin such as a polyacrylic synthetic resin, and so constituted that the emission introduced from the linear edge face is transmitted to the exit under repeated total reflection within the sheet 10. The stimulated emission from the phosphor sheet 1 is guided in the interior of the light guiding sheet 10 to the exit, and received by the light detector 11.

On the light-receiving face of the light detector 11 is provided a transfer support which allows only the light of wavelength region of the stimulated emission to pass through and cuts off the light of the wavelength region of the stimulating rays (laser beam) so as to detect only the stimulated emission. The stimulated emission detected by the light detector 11 is converted to an electric signal, amplified in an amplifier 12 and transmitted to the output. The stored information output from the amplifier 12 is supplied to a control circuit 13 of the final read-out section 3. The control circuit 13 provides an amplification degree setting value "a", a scale factor "b", and an image processing condition setting value "c", for obtaining a well readable image having uniform concentration and contrast regardless of variation of the detected information.

The phosphor sheet 1 having been subjected to the preliminary read-out in the above-described manner is then transferred to the final read-out section 3.

In the final read-out section 3, the following readout operation is performed.

The laser beam 15 generated by a laser source 14 for the final read-out passes through a filter 16 having the same function as that of the above-mentioned filter 6, and then the beam diameter is precisely adjusted in a beam expander 17. Subsequently, the laser beam is deflected by a beam deflector 18 such as a galvanometer mirror, and reflected by a plane reflection mirror 19. The deflected beam then impinges one-dimensionally upon the phosphor sheet 1. Between the beam deflector 18 and the plane reflection mirror 19 a fθ lens 20 is provided so that the beam speed is continuously kept constant, while the deflected laser beam scans the phosphor sheet 1.

The phosphor sheet 1 is transferred in the direction along the arrow 21 under the irradiation with the above-mentioned deflected laser beam. Accordingly, the whole surface of the phosphor sheet is subjected to the irradiation in the same manner as in the preliminary read-out operation.

When irradiated with the above-mentioned laser beam, the phosphor sheet 1 gives the stimulated emission in proportion to the radiation energy stored therein in the same manner as in the preliminary read-out operation. The emission then enters into a light guiding sheet 22 for the final read-out. The light guiding sheet 22 for the final read-out is made of the same material and has the same construction as the light guiding sheet 10 employed for the preliminary read-out. The stimulated emission received is guided in the interior of the light guiding sheet 22 up to the exit under repeated total reflection, and then received by a light detector 23. On the light-receiving face of the light detector 23 is provided a transfer support which allows only the light of wavelength region of the stimulated emission to pass through and cuts off the light of the wavelength region of the stimulating rays (laser beam) so as to detect only the stimulated emission.

The stimulated emission detected by the light detector 23 is converted to an electric signal, amplified to an electric signal adjusted to an appropriate level in an amplifier 24 according to the aforementioned amplification degree setting value "a" and transmitted to an A/D convertor 25. The adjusted electric signal is then converted to a digital signal in the A/D converter 25 according to an appropriate scale factor defined by the scale factor setting value "b", and then the digital signal is input into a signal processing circuit 26.

After the read-out operation of the phosphor sheet is performed on each of a phosphor sheet having one image of a radioactively labeled substance and a phosphor sheet having plural images of radioactively labeled substances (in two or more times), or after the read-out operation of the phosphor sheet is performed on three or more kinds of phosphor sheets having images of radioactively labeled substances which include a radioactively labeled substance labeled with a radioactive isotope having half-life different from others, the following subtraction processing is carried out.

In the signal processing circuit 26, the locational information (image signal) obtained by the read-out of plural phosphor sheet is once recorded in a memory (i.e., nonvolatile storage such as buffer memory or magnetic disc), the obtained digital signal is subjected to subtraction processing. In more detail, the locational information on the radioactively labeled substances is separated as to each of the radioactive isotopes by performing subtraction between locations corresponding to radiation images to be subtracted. The magnification of the subtraction is determined by calculating the thickness of the phosphor layer and the radiation energy or on the basis of a standard substance (i.e., reference) exposed together with the sample. The image signal is multiplied and the subtraction is carried out between the image signals. The subtraction processing method of a radiation image is, for example, described in Japanese Patent Provisional Publication No. 58(1983)-163340 in detail.

Subsequently, each of the locational information is processed by means of signal processing according to the image processing condition setting value "c" for obtaining a well readable visible image having appropriate density and contrast and the signals thus processed are then tranmitted to a recording device (not shown) via a data preserving means such as a magnetic tape.

Various recording devices based on various systems can be employed for the above described purpose, for instance, a device for visualizing optically by scanning a photosensitive material with laser beam, etc., a display means for visualizing electrically on CRT, etc., a means for printing radiation image displayed on CRT by means of video printer, and a means for visualizing on heat-sensitive recording material using thermic rays.

The recording device is not restricted to the visualizing devices such as mentioned above, and the one- or two-demensional information on the location of the radioactively labeled substance can be recorded, for example, in the form of numerals and/or symbols.

In the above description on the method for reading out the locational information on the radioactively labeled substances stored in the stimulable phosphor sheet, a read-out operation comprising both the preliminary read-out operation and the final read-out operation has been given. However, the read-out operation employable in the invention is not limited to the above-described embodiment. For instance, the preliminary read-out operation may be omitted if the content of the radioactive substances on the transfer support and an adequate exposure time for the transfer support is previously known.

As methods for reading out the locational information on the radioactively labeled substances stored in the stimulable phosphor sheet, it is also possible to utilize appropriate methods other than the above method.

EXAMPLE 1

An example in which the autoradiographic process of the invention is applied to the simultaneous determination of cerebral blood flow metabolism in rats is described below.

(1) Preparation of Sample

A cerebrally infracted rat after 48 hours from artery occluion and a normal rat were both prepared. 40 $\mu$Ci of $^{14}$C-2-deoxyglucose (substance for calculating consumption amounts of glucose of local brain) was administered to each of the rats through a vein according to a known method, and after 43 minutes, 2 m$\mu$Ci of N-isopropyl-p-[$^3$H] iodoamphetamine (agent for measuring blood flow of local brain) was administered in the same manner. After two minutes from the last administeration, the rats were decapitated to extract the brains and the brains were freeze-dried. The frozen brains were cut to prepare continuous sections (slices) of 20 $\mu$m as samples for analysis.

(2) Preparation of Stimulable Phosphor Sheet

On a support of polyethylene terephthalate sheet containing $TiO_2$ particles, a stimulable phosphor layer (in which divalent europium activated barium fluorobromide was dispersed in a binder of polyurethane) was formed to prepare a stimulable phosphor sheet A.

Similarly, a stimulable phosphor layer (in which the same divalent europium activated barium fluorobromide was dispersed in a binder of polyurethane) was formed on a support of polyethylene terephthalate sheet containing $TiO_2$ particles, and a transparent polyethylene terephthalate sheet (protective layer; thickness 20 $\mu$m) was coated over a surface of the phosphor layer to prepare a stimulable phosphor sheet B.

(3) Autoradiography

One of the samples (i.e., cerebrally infracted rat and normal rat) was placed on the stimulable phosphor sheet A for 12 hours for performing exposure. Subsequently, another sample was placed on the stimulable phosphor sheet B for 12 hours for performing exposure.

The stimulable phosphor sheets A and B (four sheets in total) subjected to the exposing procedure using the cerebrally infracted rat and normal rat were subjected to the read-out operation using the read-out system shown in FIG. 1 to obtain the autoradiogram. As for each sample of the cerebrally infracted rat and normal rat, the locational information signals corresponding to the autoradiogram obtained from the stimulable phosphor sheet A and those obtained from the stimulable phosphor sheet B were subjected to a subtraction processing, and distribution of each of $^{14}$C-2-deoxyglucose and N-isopropyl-p-[$^3$H] iodoamphetamine per each sample was examined. As a result, the distributions obtained from the sample of the normal rat showed that consumption amounts of glucose of local brain and blood flow of local brain well coincided with each other, while the distributions obtained from the sample of the the cerebrally infracted rat showed that consumption amounts of glucose of local brain and blood flow of local brain did not coincide with each other.

EXAMPLE 2

(1) Preparation of Sample

A local myocardial ischemia-model rat after 30 minutes from artery occluion and a normal rat were prepared. 1 mCi of $^3$H-2-deoxyglucose (substance for calculating consumption amounts of glucose of local heart) and 20 μCi of $^{14}$C-β-methylheptadecanic acid ($^{14}$C-BMHDA; substance for calculating consumption amounts of free fatty acid of local heart) were administered to each of the rats by intravenous injection according to the known method. After 30 minutes, 2 mCi of $^{123}$I-p-iodoamphetamine (agent for measuring blood flow of local brain) was administered in the same manner and the rats were slaughtered. The hearts were extracted and were freeze-dried. The frozen hearts were cut to prepare continuous sections (slices) of 20 μm as samples for measurement.

(2) Preparation of Stimulable Phosphor Sheet

On a support of polyethylene terephthalate sheet containing TiO$_2$ particles, a stimulable phosphor layer (in which divalent europium activated barium fluorobromide was dispersed in a binder of polyurethane) was formed to prepare a stimulable phosphor sheet A.

Similarly, a stimulable phosphor layer (in which the same divalent europium activated barium fluorobromide was dispersed in a binder of polyurethane) was formed on a support of polyethylene terephthalate sheet containing TiO$_2$ particles, and a transparent polyethylene terephthalate sheet (protective layer; thickness 20 μm) was coated over a surface of the phosphor layer to prepare a stimulable phosphor sheet B.

(3) Autoradiography

Immediately after preparation of the samples, one of the samples (sections of hearts of a local myocardial ischemia-model rat and a normal rat) was palced on the stimulable phosphor sheet A for 12 hours for performing exposure. Subsequently, another sample was placed on the stimulable phosphor sheet B for 12 hours.

After the samples (sections of hearts of a local myocardial ischemia-model rat and a normal rat) were allowed to stand for two months, one of the samples was placed on the stimulable phosphor sheet A for 12 hours for performing exposure. Subsequently, another sample was placed on the stimulable phosphor sheet B were placed in layers for 12 hours.

The stimulable phosphor sheets A and B (eight sheets in total) subjected to the exposing procedure using the local myocardial ischemia-model rat and normal rat were subjected to the read-out operation using the read-out system shown in FIG. 1 to obtain autoradiograms. As for each sample of the local myocardial ischemia-model rat and normal rat, the locational information signals corresponding to the autoradiograms obtained from the stimulable phosphor sheet A and the stimulable phosphor sheet B immediately after preparation of the samples, and the locational information signals corresponding to the autoradiograms obtained from the stimulable phosphor sheet A and those obtained from the stimulable phosphor sheet B after two months were subjected to a subtraction processing, and distribution of each of $^3$H-2-deoxyglucose, $^{14}$C-β-methylheptadecanic acid and $^{123}$I-p-iodoamphetamine per each sample was observed.

As a result, the distributions obtained from the sample the local myocardial ischemia-model rat showed that both amounts of blood flow and sugar uptake were extremely decreased in a center area of ischemia, and amounts of sugar uptake were in a normal region or rather increased in spite of decrease of blood flow in a verge area and subendocardial area. Further, it was apparent that amounts of free fatty acid were extremely decreased, compared with amounts of sugar uptake in a ischemia area.

We claim:

1. An autoradiographic process for obtaining locational information on at least two kinds of radioactively labeled substances which are labeled with radioactive isotopes having mean energies different from each other, said radioactively labeled substances being contained in a sample selected from the group consisting of tissue of an organism and a medium containing tissue of an organism or substances originating from an organism, which comprises:

(1) a step of placing said sample on a stimulable phosphor sheet comprising a phosphor layer and a protective polymer layer coated and fixed thereon for a given period of time to cause the phosphor layer to absorb radiation energy emitted by the radioactively labeled substance having a higher mean energy;

(2) a step of obtaining an image signal showing locational information on the radioactively labeled substance having a higher mean energy, which comprises exciting the phosphor layer of the stimulable phosphor sheet with an electromagnetic wave to release the radiation energy stored in said phosphor layer as stimulated emission and detecting the stimulated emission;

(3) a step of placing said sample on a stimulable phosphor sheet comprising a phosphor layer on which no protective layer is provided or a thinner protective polymer layer than the protective polymer layer employed in the step (1), via the thinner or no protective layer, for a given period of time to cause said phosphor layer to absorb radiation energy emitted by both a radioactively labeled substance having a higher mean energy and one having a lower mean energy;

(4) a step of obtaining an image signal showing locational information of both the radioactively labeled substance having a higher mean energy and one having a lower mean energy, which comprises exciting said phosphor layer of said stimulable phosphor sheet having been subjected to the step (3) with an electromagnetic wave to release the radiation energy stored in the phosphor layer as stimulated emission and detecting the stimulated emission; and (5) a step of obtaining locational information on each of at least two kinds of radioactively labeled substances contained in said sample, which comprises subjecting the image signal obtained in the steps (2) and (4) to a subtraction processing for eliminating the image signal obtained in the step (2) from that obtained in the step (4).

2. The autoradiographic process defined in claim 1, wherein said radioactively labeled substances are radioactively labeled with radioactive isotopes selected from the group consisting of $^3H$, $^{123}I$, $^{131}I$, $^{14}C$, $^{35}S$, $^{18}F$, and $^{32}P$.

3. The autoradiographic process defined in claim 1, wherein the radioactively labeled substance having a higher mean energy is labeled with $^{14}C$ and the radioactively labeled substance having a lower mean energy is labeled with $^3H$.

4. An autoradiographic process for obtaining locational information on at least two kinds of radioactively labeled substances which are labeled with radioactive isotopes having mean energies different from each other and a radioactively labeled substance which is labeled with a radioactive isotope having a half-life different from that of at least one of the former radioactive isotopes, all the radioactively labeled substances being contained in a sample selected from the group consisting of tissue of an organism and a medium containing tissue of an organism or substances originating from an organism, which comprises:

(I) a procedure for obtaining at least three image signals by performing at least three steps of the following four steps (1) to (4):

(1) a step of obtaining an image signal showing locational information on the radioactively labeled substance having a higher mean energy, which comprises placing the sample on a stimulable phosphor sheet comprising a phosphor layer and a protective polymer layer coated and fixed thereon for a given period of time to cause the phosphor layer to absorb radiation energy emitted by the radioactively labeled substance having a higher mean energy, subsequently exciting the phosphor layer of the stimulable phosphor sheet with an electromagnetic wave to release the radiation energy stored in the phosphor layer as stimulated emission and detecting the stimulated emission;

(2) a step of obtaining an image signal showing locational information on both the radioactively labeled substance having a higher mean energy and one having a lower mean energy, which comprises placing the sample on a stimulable phosphor sheet comprising a phosphor layer on which no protective layer is provided or a thinner protective polymer layer than the protective polymer layer employed in the step (1) is coated and fixed, via the thinner or no protective layer, for a given period of time to cause the phosphor layer to absorb radiation energy emitted by both the radioactively labeled substance having a higher mean energy and one having a lower mean energy, subsequently exciting the phosphor layer of the stimulable phosphor sheet with an electromagnetic wave to release the radiation energy stored in the phosphor layer as stimulated emission and detecting the stimulated emission;

(3) a step of obtaining an image signal showing locational information on the radioactively labeled substance having a higher mean energy, which comprises allowing the sample to stand for a period determined on the basis of the shortest half-life of the radioactive isotope contained in the sample, thereafter placing the sample on a stimulable phosphor sheet comprising a phosphor layer and a protective polymer layer thereon for a given period of time to cause the phosphor layer to absorb radiation energy emitted by the radioactively labeled substance having a higher mean energy, subsequently exciting the phosphor layer of the stimulable phosphor sheet with an electromagnetic wave to release the radiation energy stored in the phosphor layer as stimulated emission and detecting the stimulated emission; and (4) a step of obtaining an image signal showing locational information on both the radioactively labeled substance having a higher mean energy and one having a lower mean energy, which comprises allowing the sample to stand for a period determined on the basis of the shortest half-life of the radioactive isotope contained in the sample, thereafter placing the sample on a stimulable phosphor sheet comprising a phosphor layer on which no protective layer is provided or a thinner protective polymer layer than the protective polymer layer employed in the step (3) is provided, via the thinner or no protective layer, for a given period of time to cause the phosphor layer to absorb radiation energy emitted by both the radioactively labeled substance having a higher mean energy and one having a lower mean energy, subsequently exciting the phosphor layer of the stimulable phosphor sheet with an electromagnetic wave to release the radiation energy stored in the phosphor layer as stimulated emission and detecting the stimulated emission; and (II) a procedure of obtaining each of locational information on at least three kinds of radioactively labeled substances contained in the sample, which comprises subjecting the image signals obtained in the procedure (I) to a subtraction processing.

5. The autoradiographic process defined in claim 4, wherein said radioactively labeled substances are radioactively labeled with radioactive isotopes selected from the group consisting of $^3H$, $^{123}I$, $^{131}I$, $^{14}C$, $^{35}S$, $^{18}F$, and $^{32}P$.

6. The autoradiographic process defined in claim 4, wherein the radioactively labeled substance having a higher mean energy is labeled with $^{14}C$, the radioactively labeled substance having a lower mean energy is labeled with $^3H$, and the other is labeled with $^{123}I$.

* * * * *